(12) United States Patent
Hee-Hanson et al.

(10) Patent No.: US 12,274,866 B1
(45) Date of Patent: Apr. 15, 2025

(54) ROTATABLE COLLAR FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/620,210

(22) Filed: Mar. 28, 2024

(51) Int. Cl.
*A61M 5/315* (2006.01)
*A61M 5/20* (2006.01)

(52) U.S. Cl.
CPC .......... *A61M 5/31536* (2013.01); *A61M 5/20* (2013.01); *A61M 2005/2013* (2013.01)

(58) Field of Classification Search
CPC ............... A61M 5/31536; A61M 5/20; A61M 5/31535; A61M 5/31533; A61M 5/31511; A61M 5/31505; A61M 5/48; A61M 5/484; A61M 2005/3151; A61M 2005/3143; A61M 2005/2013
See application file for complete search history.

(56) References Cited

U.S. PATENT DOCUMENTS

| | | | |
|---|---|---|---|
| 4,900,311 | A | 2/1990 | Stern et al. |
| 5,088,986 | A | 2/1992 | Nusbaum |
| 5,290,256 | A | 3/1994 | Weatherford et al. |
| 5,688,241 | A | 11/1997 | Asbaghi |
| 7,597,685 | B2 | 10/2009 | Olson |
| 8,016,797 | B2 | 9/2011 | Gratwohl et al. |
| 8,821,451 | B2 | 9/2014 | Daniel |
| 9,199,038 | B2 | 12/2015 | Daniel |
| 9,408,976 | B2 | 8/2016 | Olson et al. |
| 9,498,579 | B2 | 11/2016 | Ruan |
| 9,662,452 | B2 | 5/2017 | Daniel |

(Continued)

FOREIGN PATENT DOCUMENTS

| WO | WO 2011/123024 A1 | 10/2011 |
|---|---|---|
| WO | WO 2014/115241 A1 | 7/2014 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Tasnim Mehjabin Ahmed
(74) *Attorney, Agent, or Firm* — Fish & Richardson P.C.

(57) ABSTRACT

An injection device comprising: an injection device body; a plunger comprising one or more plunger recesses; biasing means for applying a biasing force to bias the plunger in a distal direction of the injection device; a casing at least partially enclosing the plunger, the casing comprising one or more toothed beams each comprising a tooth engageable with a corresponding plunger recess of the one or more plunger recesses; and a rotatable collar at least partially enclosing the casing and comprising one or more collar recesses on an inner surface of the rotatable collar.

25 Claims, 6 Drawing Sheets

(56) References Cited

U.S. PATENT DOCUMENTS

| | | |
|---|---|---|
| 9,867,940 B2 | 1/2018 | Holmqvist et al. |
| 9,919,107 B2 | 3/2018 | Imai et al. |
| 10,420,898 B2 | 9/2019 | Daniel |
| 11,369,751 B2 | 6/2022 | Ruan et al. |
| 11,944,787 B2 | 4/2024 | Franke |
| 2006/0276756 A1 | 12/2006 | Francavilla |
| 2010/0268170 A1 | 10/2010 | Carrel et al. |
| 2012/0203186 A1 | 8/2012 | Vogt et al. |
| 2013/0041328 A1 | 2/2013 | Daniel |
| 2013/0096512 A1 | 4/2013 | Ekan et al. |
| 2013/0123710 A1 | 5/2013 | Ekman et al. |
| 2013/0261559 A1 | 10/2013 | Werbickas |
| 2014/0025013 A1 | 1/2014 | Dowds et al. |
| 2015/0190580 A1 | 7/2015 | Imai et al. |
| 2015/0258283 A1 | 9/2015 | Imai et al. |
| 2016/0089498 A1 | 3/2016 | Daniel |
| 2018/0064875 A1 | 3/2018 | Holmqvist |
| 2018/0361082 A1 | 12/2018 | Sall et al. |
| 2020/0289755 A1* | 9/2020 | Franke ................ A61M 5/2033 |
| 2021/0236732 A1 | 8/2021 | Chu et al. |
| 2021/0244887 A1 | 8/2021 | Halseth |
| 2021/0393886 A1* | 12/2021 | Nicolas ................. A61M 5/24 |
| 2022/0387719 A1 | 12/2022 | Wang et al. |
| 2022/0395642 A1 | 12/2022 | Karlsson |
| 2024/0139430 A1 | 5/2024 | Chansavang et al. |
| 2024/0165346 A1 | 5/2024 | Chansavang et al. |

FOREIGN PATENT DOCUMENTS

| | | |
|---|---|---|
| WO | WO 2021/008839 A1 | 1/2021 |
| WO | WO 2023/104512 A1 | 6/2023 |

OTHER PUBLICATIONS

U.S. Appl. No. 18/619,754, filed Mar. 28, 2024, Alexander Hee-Hanson.

U.S. Appl. No. 18/619,991, filed Mar. 28, 2024, Alexander Hee-Hanson.

U.S. Appl. No. 18/620,586, filed Mar. 28, 2024, Alexander Hee-Hanson.

U.S. Appl. No. 18/619,996, filed Mar. 28, 2024, Alexander Hee-Hanson.

U.S. Appl. No. 18/620,097, filed Mar. 28, 2024, Alexander Hee-Hanson.

* cited by examiner

ROTATABLE COLLAR FOR INJECTION DEVICES

TECHNICAL FIELD

This application relates to an injector device for delivery of a medicament, particularly to an auto-injector device.

BACKGROUND

An auto-injector may be described as a device which completely or partially replaces the activities involved in parenteral drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle cover which is biased by a spring (the needle cover spring) to extend out of the device. On removal of the device from the injection site, this spring automatically extends the needle cover past the needle to provide needle shielding. On activation of the device, the needle cover is pushed into the device. A user has to provide the force to actuate the needle cover, overcome the activation mechanism forces and compress the needle cover spring (activation force). During drug delivery the user must hold the device at the injection site and apply a force (hold force) parallel to the needle cover direction of extension to react the needle cover biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This results in pain, discomfort, a wet injection site, early device removal and partial drug delivery.

SUMMARY

According to a first aspect of this specification, an injection device includes: an injection device body; a plunger including one or more plunger recesses; biasing means for applying a biasing force to bias the plunger in a distal direction of the injection device; a casing at least partially enclosing the plunger, the casing including one or more toothed beams each including a tooth engageable with a corresponding plunger recess of the one or more plunger recesses; and a rotatable collar at least partially enclosing the casing and including one or more collar recesses on an inner surface of the rotatable collar; and wherein: each of the one or more plunger recesses is shaped to urge a tooth of the corresponding toothed beam outwards when the biasing force is applied to the plunger in a pre-use configuration; and the one or more collar recesses are shaped to cooperate with a tooth of a corresponding toothed beam to apply a torque to the rotatable collar when the corresponding toothed beam is urged outwards in the pre-use configuration.

The rotatable collar may further include a cam track on an outer surface of the rotatable collar. The injection device may further include a needle shroud retractable into the injection device and including a shroud pin engageable with the cam track of the rotatable collar. The cam track is shaped to guide the shroud pin from an initial position to a hold position and cause the collar to rotate relative to the injection device body during retraction of the needle shroud. The cam track may include an initial portion aligned with the biasing force direction and including a retaining edge arranged to contact the shroud pin in the pre-use position to prevent rotation of the collar with respect to the plunger and/or casing. The cam track may include an angled portion arranged to contact the shroud pin for at least a part of the retraction of the needle shroud, thereby applying a torque to the rotatable collar during retraction of the needle shroud. The cam track may further include a final portion for guiding the shroud pin from the hold position to a final position, the final portion including a locking mechanism to prevent retraction of needle shroud after the shroud pin has reached the final position.

The one or more teeth of the one or more toothed beams may be chamfered in the distal direction.

Each tooth may extend inwardly in a radial direction from the respective toothed beam. An outside surface of each tooth may be chamfered in an axial direction to form a tooth contact surface for contacting the recess in a pre-use configuration. The one or more collar recesses may each include a collar contact surface for contacting the tooth contact surface of the respective tooth in the pre-use configuration. Each collar contact surface may include a curved surface that has a radial depth that increases in the opposite direction to the rotation direction of the collar.

The one or more plunger recesses may include a curved edge at a proximal end of the plunger recess.

The one or more plunger recesses may include a plurality of plunger recesses arranged evenly around the plunger in an angular/azimuthal direction. The one or more toothed beams may include a corresponding plurality of toothed beams arranged evenly around the casing in the angular/azimuthal direction. The one or more collar recesses may include a corresponding plurality of collar recesses arranged evenly around the inside surface of the collar in the angular/azimuthal direction.

The injection device may further include a needle for expelling medicament from a medicament cartridge.

The injection device may further include a medicament cartridge containing a medicament.

According to a further aspect of this specification, a tubular collar for an injection device includes: an outer surface; an inner surface; one or more collar recesses on the inner surface of the tubular collar, the one or more collar recesses are shaped to cooperate with a tooth of a corresponding toothed beam of an injection device casing to apply a torque to the tubular collar when the corresponding toothed beam is urged outwards; and a cam track on the outer surface of the rotatable collar wherein the cam track is shaped to guide a shroud pin of a needle shroud from an initial position to a hold position and apply a torque to the tubular collar during retraction of the needle shroud.

The cam track may include an initial portion aligned with the biasing force direction and including a retaining edge arranged to contact the shroud pin in the pre-use position to prevent rotation of the collar with respect to the plunger and/or casing. The cam track may include an angled portion arranged to contact the shroud pin for at least a part of the retraction of the needle shroud, thereby applying a torque to the rotatable collar during retraction of the needle shroud. The cam track may further include a final portion for guiding the shroud pin from the hold position to a final position, the final portion including a locking mechanism to prevent retraction of needle shroud after the shroud pin has reached the final position.

The one or more collar recesses may each include a collar contact surface for contacting the tooth contact surface of the respective tooth of a corresponding toothed beam in the pre-use configuration. Each collar contact surface may include a curved surface that has a radial depth that increases in the opposite direction to the rotation direction of the collar. According to a further aspect of this specification, a method for reducing a peak activation force of an injection device includes: in a pre-use configuration of the injection device: applying a biasing force in a distal direction to a plunger of the injection device; converting the biasing force into a respective outward radial force on one or more toothed beams of a casing of the injection device using a corresponding one or more recesses of the plunger in cooperation with a respective one or more teeth of the toothed beams; converting at least a part of the respective outward radial forces on the one or more toothed beams to a torque on a rotatable collar of the injection device using one or more collar recesses in cooperation with a respective one or more of the teeth of the toothed beams; and retaining the plunger in the pre-use position by preventing rotation of the rotatable collar using a first portion of a cam track on the rotatable collar; during retraction of a needle shroud into an injection device body, guiding a shroud pin of a needle shroud from an initial position to a hold position using the first portion of the cam track and a ramped portion of the cam track, the guiding causing the rotatable collar to rotate relative to an injection device body, wherein rotation of the rotatable collar causes one or more collar recesses to align with the respective one or more teeth of the toothed beam, thereby releasing the plunger.

The cam track may include an initial portion aligned with the biasing force direction and including a retaining edge arranged to contact the shroud pin in the pre-use position to prevent rotation of the collar with respect to the plunger and/or casing. The cam track may include an angled portion arranged to contact the shroud pin for at least a part of the retraction of the needle shroud, thereby applying a torque to the rotatable collar during retraction of the needle shroud.

The method may further include: guiding the shroud pin from the hold position to a final position using a final portion of the cam track; and locking the shroud pin at the final position using a locking mechanism to prevent retraction of needle shroud after the shroud pin has reached the final position The biasing force may be applied using a drive spring of the injection device.

The method may further including expelling, by the plunger and after the plunger is released, medicament from a medicament cartridge of the injection device.

Throughout this specification, use of the injection device is described in terms of a user, who operates the injection device, and a subject, who receives an injection from the injection device. The user and the subject may be the same person. Alternatively, the user and subject may be different entities, e.g., a healthcare provider and a patient.

BRIEF DESCRIPTION OF THE DRAWINGS

Embodiments are described with reference to the accompanying drawings.

DETAILED DESCRIPTION

A drug delivery device, as described herein, may be configured to inject a medicament into a subject. For example, delivery could be sub-cutaneous, intra-muscular, or intravenous. Such a device could be operated by a subject or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence drug delivery. One of these actions apply an axial force to the device by either pushing a needle cover into the device or pressing a button on the device. The axial force required is referred to as the activation force in this document. The magnitude and profile of this activation force has an impact on the usability of the device.

After the device is removed from the user's body post use, many autoinjectors cover the needle with a shroud/needle cover, which is extended out of the device by a control spring. This shroud is locked in its extended position by a needle cover locking mechanism, often featuring a one-way clip feature. The control spring must have enough force to ensure this mechanism is activated following device removal. The user must react the control spring force during activation and hold. It may be beneficial to reduce the hold and/or activation force. Reducing the force to active the needle cover locking mechanism, enables a reduction in the control spring and therefore reduces the hold and activation forces.

To activate injection devices described herein, a user pushes a needle shroud into the device. A pin on the shroud pushes against a ramped surface on a cam track of the collar to rotate it, allowing a set of rear case clips to flex outwards, which releases the plunger. To activate the device the user must overcome the frictional force between the collar and the rear case clips, which dictates the activation force.

Injection devices described herein use a further ramped surface between the rear case clips (also referred to herein as "toothed beams") and the plunger to transfer some of a drive spring force to a collar rotation torque so the user no longer has to provide the energy to rotate the collar during activation, reducing the activation force.

This can result in a more constant force profile during activation, and a reduction in the peak activation force, making the device easier to use for a user and thereby reducing pain, discomfort, instances of a wet injection site, early device removal and partial drug delivery.

Figure 1:
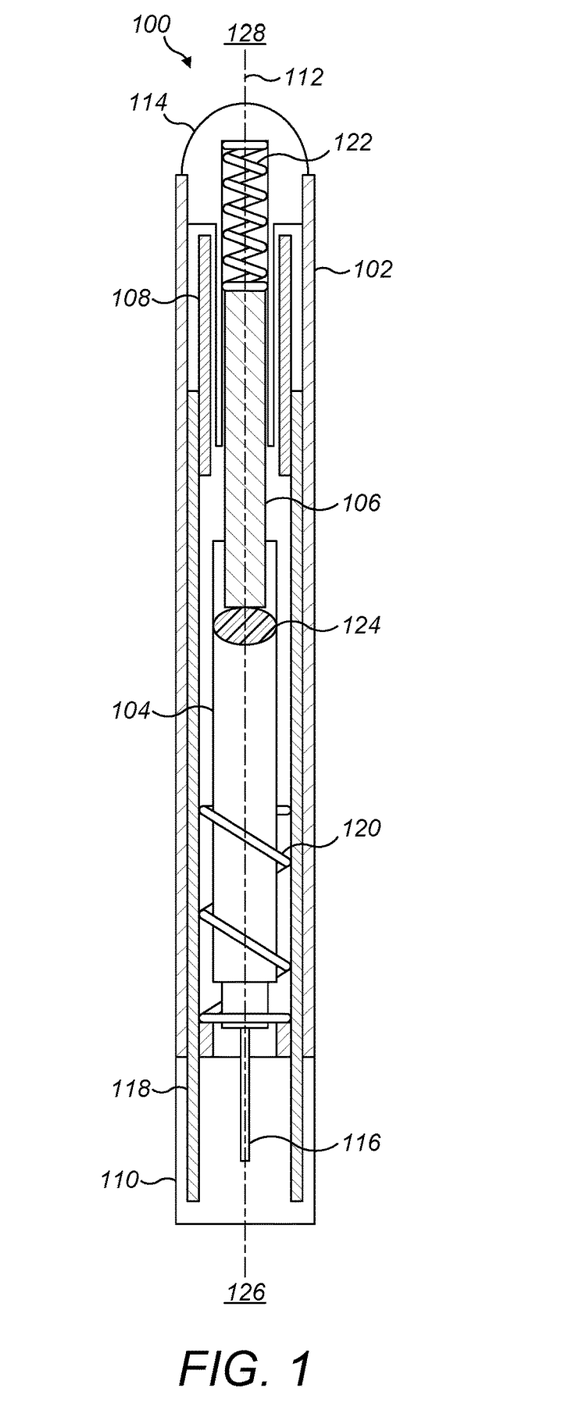
FIG. 1 shows a schematic example of a cross section of an injection device.

FIG. 1 shows a schematic example of a cross section of an injection device 100. The injection device is configured to inject a medicament into a subject's body. The injection device 100 includes an outer casing 102 (also referred to as an "injection device body") that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user must remove cap 110 from the outer casing 102 before device 100 can be operated.

As shown, the outer casing 102 is substantially cylindrical and has a substantially constant diameter along the longitudinal axis of the device 100. The injection device 100 has a distal region and a proximal region. The term "distal" refers to a location that is relatively closer to a site of injection (i.e. the needle end of the injection device 100), and the term "proximal" refers to a location that is relatively further away from the injection site.

The outer casing 102 is closed at a proximal end by a rear casing 114 (also referred to herein as a "casing"). The rear casing 114 includes a cap at the proximal end of the injection device body, and a tubular extension that extends into the injection device body. The tubular extension includes one or more rear case clips (also referred to herein as "toothed beams") for retaining the plunger 106 in position in a pre-use configuration.

A needle 116 and a retractable needle shroud 118 (also referred to as a "needle sleeve" or "needle cover") extend from a distal end of the outer casing 102. The retractable needle shroud 118 is biased in the distal direction of the injection device 100, for example using a control spring 120. The needle shroud 118 is coupled to the outer casing 102 to permit movement of needle shroud 118 relative to the outer casing 118. For example, the shroud 118 can move in a longitudinal direction parallel to longitudinal axis 112. Specifically, movement of shroud 118 in a proximal direction can permit a needle 116 to extend from distal region of the casing 102. In some examples, rotational motion of the needle shroud 118 relative to the injection device body is restricted, e.g., completely prevented.

The plunger 106 is biased towards the distal end of the injection device 100 by a biasing means, for example using a drive spring 122. The plunger 106 is retained in an initial position by a combination of the clips of the rear casing 114 and the collar 108, preventing the biasing means from displacing the plunger 106 in the distal direction when in the pre-use configuration. An example of such a retention mechanism is described in relation to FIGS. 2 to 4B. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle shroud 118. Proximal movement of shroud 118 by placing a distal end of the shroud 118 against a subject's body and moving casing 102 in a distal direction will uncover the distal end of the needle 116. Such relative movement allows the distal end of the needle 118 to extend into the subject's body. Such insertion is termed "manual" insertion as the needle 118 is manually inserted via the subject's manual movement of the casing 102 relative to shroud 118. Retraction of the shroud 118 into the casing 102 causes the collar 108 to rotate, releasing the plunger 106.

Another form of activation is "automated," whereby the needle 116 moves relative to casing 102. Such insertion can be triggered by movement of the shroud 118 and/or by another form of activation, such as, for example, a button (not shown).

Typically, the user presses the needle shroud 118 against an injection site to push the needle shroud 118 at least partially into the device body. The exposed needle 116 is pushed into the injection site. In a holding position, medicament is automatically dispensed from the needle 116 via an automated mechanism. A user must typically hold the needle shroud 118 in the holding position for a predetermined period of time, to ensure that the correct dose of medicament is dispensed from the device 100, before removing the device from the injection site.

The spring force from the control spring 120 against which the user must apply a force to move the needle shroud 118 is one component of an "activation force" of the device 100. The activation force refers to the force or force profile that the user must exert on the device 100 to move the needle shroud 118 from the extended position shown in FIG. 1 to a retracted position. If this force or force profile is not well balanced, it can lead to difficulty in activating the device 100 for some users, or increase the pain or anxiety associated with using the device.

Following injection, the needle 116 can be retracted within the shroud 118. Retraction can occur when the shroud 118 moves distally under the biasing of the control spring 120 as a user removes the device 100 from a subject's body. Once a distal end of shroud 118 has moved past a distal end of the needle 116, and the needle 116 is covered, and the shroud 118 is locked. Such locking can include locking any (substantial) proximal movement of the shroud 118 relative to the casing 102, i.e., preventing any movement of the shroud 118 that would uncover the needle.

Figure 2:
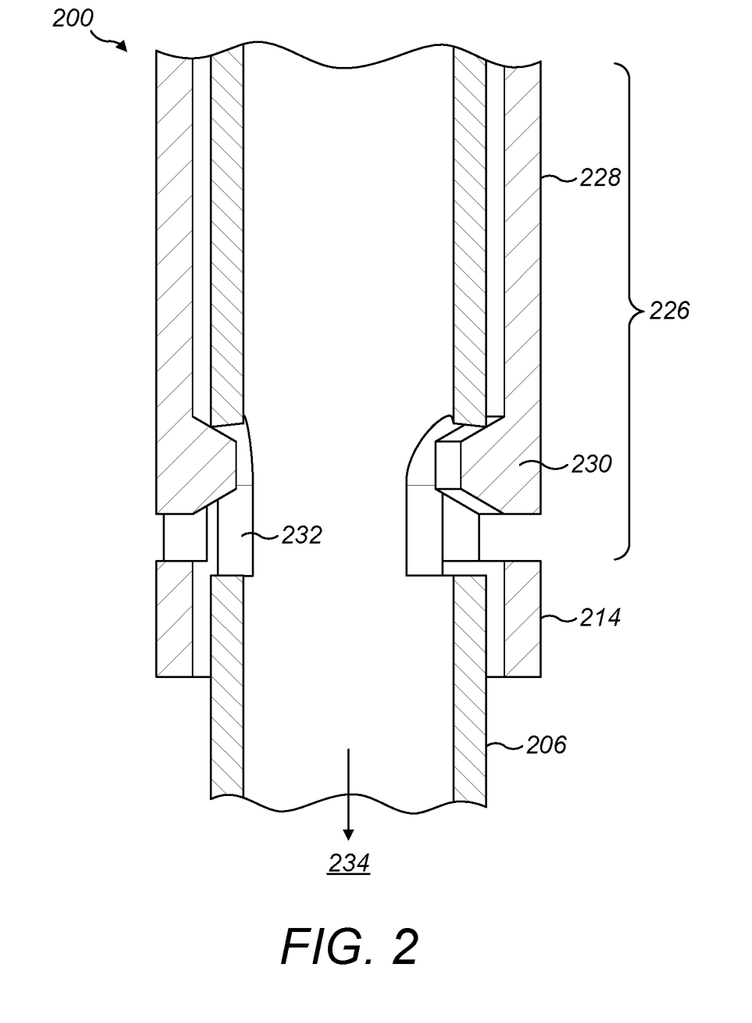
FIG. 2 shows a cut-away view of an example retention mechanism for a plunger.

FIG. 2 shows a cut-away view of an example retention mechanism 200 for a plunger 206. The plunger 206 is retained in place pre-activation by one or more toothed beams 226 of the rear casing 214 (i.e., rear casing clips), in cooperation with a collar (not shown). The rear casing 214 includes one or more (e.g., two or three) toothed beams 226. Each toothed beam 226 includes a flexible arm 228, e.g., an elongated arm, and a tooth 230. Each tooth 230 is at a distal end of its respective flexible arm 228 and extends inwards radially from its respective flexible arm 228. The plunger 206 includes a corresponding one or more recesses 232 (also referred to herein as "plunger recesses") which can each engage with a respective tooth 230 of a respective toothed beam 226. In some examples, the recesses 232 and toothed beams 226 are evenly spaced around the plunger 206 and rear casing 214 respectively, e.g., spaced at 180 degrees around the plunger 206 and rear casing 214 for two recesses and teeth, spaced at 120 degrees around the plunger 206 and rear casing 214 for three recesses and teeth, etc. While held in the recesses 230 (e.g., by the collar, as described in relation to FIGS. 3A and 3B), the teeth 230 of the toothed beams 226 prevent the plunger 206 from moving in the distal direction 232 under the biasing force 234 of the drive spring.

The one or more recesses 232 and/or corresponding teeth 230 are shaped to urge the toothed beams 226 outwards when a force 234 is applied to the plunger 206 in the distal direction. For example, each tooth 430 may include a ramped surface/bevel (e.g., be chamfered) at its proximal end (and may, in some examples also be bevelled at its distal end). When the plunger 206 moves/is urged in the distal direction (e.g., under the force 234 of the driving spring), an upper (i.e., proximal portion) of each recess 232 contacts the bevel of its respective tooth 230 and applies an outward force to the respective toothed beam 226. In the absence of retention, e.g., by a collar, this causes the toothed beams 226 to flex outwards, releasing the plunger 206 and allowing an injection to proceed.

The one or more recesses 232 extend into the surface of the plunger 206, e.g., in a radial direction. In some examples, the one or more recesses 232 each extend completely through the wall of the plunger 206, i.e., are in the form of holes in the plunger wall, as shown in FIG. 2. Alternatively, the one or more recesses 223 each extend partially through the plunger wall, i.e., are indentations in the plunger wall. In some examples with a plurality of recesses, one or more of the recesses 232 extend fully through the plunger wall and one or more recesses 232 partially extend through the plunger wall. In some examples, the proximal end of each recess 232 is curved.

Figure 3A:
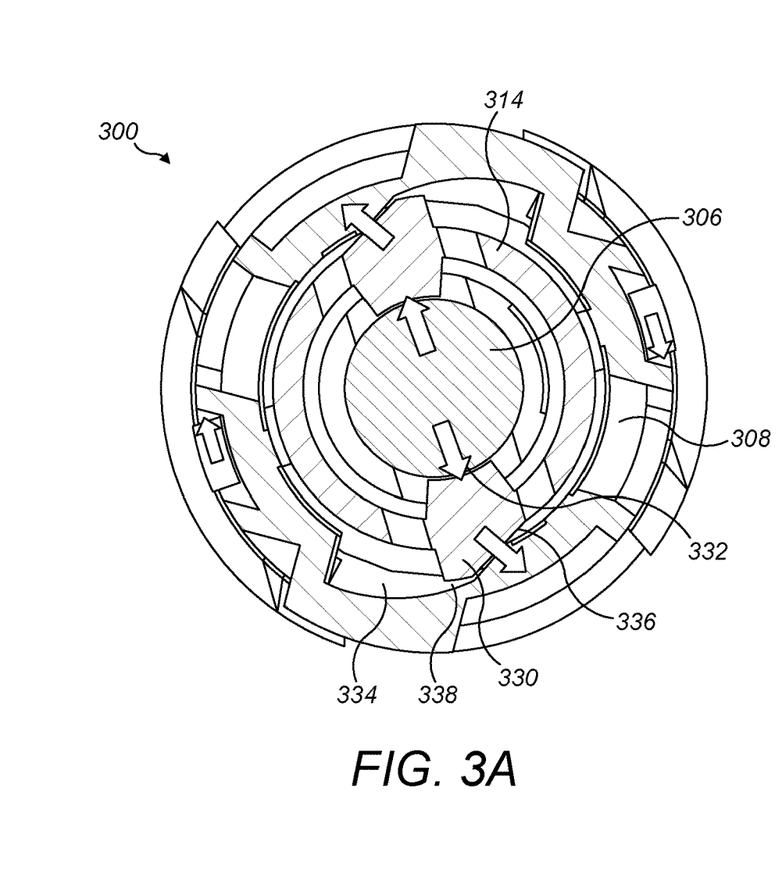
FIG. 3A shows a cross section view of an example retention mechanism for a plunger in a pre-activation configuration.

FIG. 3A shows a cross section view of an example retention mechanism 300 for a plunger 306 in a pre-activation configuration. The view is from the proximal end of the injection device looking in the distal direction. A portion of a rear casing 314 surrounds the outer axial surface of the plunger 306, with one or more teeth 330 of one or more respective flexible arms of the rear casing 314 engaging with a respective one or more plunger recesses 332 of the plunger 306, as shown and described in relation to in FIG. 2. A portion of the rear casing 314 including toothed beams is at least partially surrounded by a rotatable collar 308. In some examples, the portion of the rear casing 314 including toothed beams is fully surrounded by the rotatable collar 308.

The rotatable collar 308 includes one or more collar recesses 334 on an inner surface of the rotatable collar 308 for receiving a respective tooth 330 of a toothed beam of the casing 314. Each collar recess 334 is shaped to cooperate with a corresponding tooth 330 such that the collar recess 334 converts an outward radial force applied by the corresponding tooth 330 into a torque on the collar 308. Each collar recess 334 is arranged to generate a torque on the collar 308 in (substantially) the same direction. In the example shown, the torque acts rotate the collar 308 in an anti-clockwise direction.

In the example shown, the portion of the casing 314 surrounding the plunger is substantially cylindrical (i.e., tubular), and has two toothed beams arranged on opposing sides of the casing 314. The plunger 306 in this example is at least in part substantially cylindrical, with two plunger recesses 332 arranged on opposing sides of the plunger body. The two plunger recesses 332 are aligned with corresponding teeth 330 of the toothed beams in this pre-use configuration.

The outside (i.e., collar-facing side) of each tooth 330 includes a ramped contact surface 336 for contacting a corresponding ramped contact surface 338 of the corresponding recess 334 of the collar 308. The ramped contact surface 336 may be chamfered in an axial direction. The ramped contact surface 336 of the tooth 330 and the ramped contact surface 338 of the recess 334 cooperate to apply a torque to the collar 308 when an outward radial force is applied to the tooth. This angled interface between the rear casing clips and the collar converts the radial clip force into a collar torque.

The ramped contact surface 338 of the collar recess 334 may include a curved surface. The curved surface results in a depth of the recess 334 varying around the collar. For example, the curved surface is shaped to increase the radial depth of the recess in the opposite direction of the collar rotation direction, i.e., as the collar rotates, deeper parts of the recess 334 align with the corresponding tooth 330.

As described in relation to FIG. 0.2, the recesses 314 of the plunger 306 and/or the teeth 330 of the rear casing clips are shaped to urge the teeth 330 outwardly in the radial direction. The contact surface 336 of the teeth 330 contact the corresponding contact surfaces 338 of the collar recesses 334 under this outward force, e.g., at the angled interface. Due to the angling of both contact surfaces 336, 338, the outward force applied to the collar contact surface 338 by the corresponding tooth contact surface 336 is converted to a torque on the collar 308. In the absence of any retention mechanism, this would cause the collar 308 to rotate relative to the casing 314 and plunger 306 (and to the injection device body). However, as described in relation to FIG. 3B, a shroud pin of the needle shroud prevents the collar 308 rotating until the shroud retraction has reached an activated position.

Figure 3B:
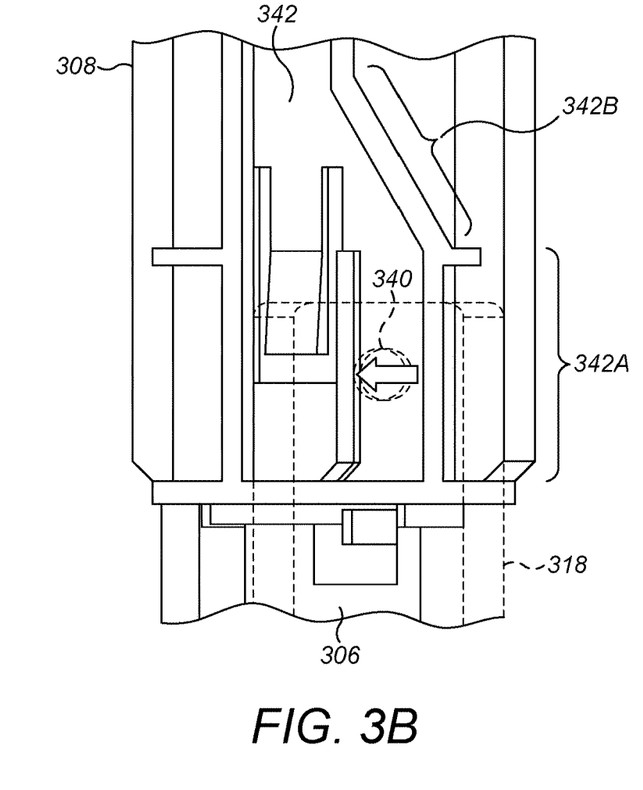
FIG. 3B shows a side view of the outside of an example retention mechanism for a plunger in a pre-activation configuration.

FIG. 3B shows a side view of the outside of an example retention mechanism 300 for a plunger 306 in a pre-activation configuration.

As described in relation to FIG. 1, the injection device includes a needle shroud 318 that is retractable into the body of the injection device. Rotation of the needle shroud 318 with respect to the injection device body is restricted, e.g., no rotation of the needle shroud 318 with respect to the injection device body is permitted. The needle shroud 318 includes a shroud pin 340 that extends inwardly from the needle shroud 318. The shroud pin 340 engages with a cam track 342 on an outside surface of the rotatable collar 308.

Figure 4A:
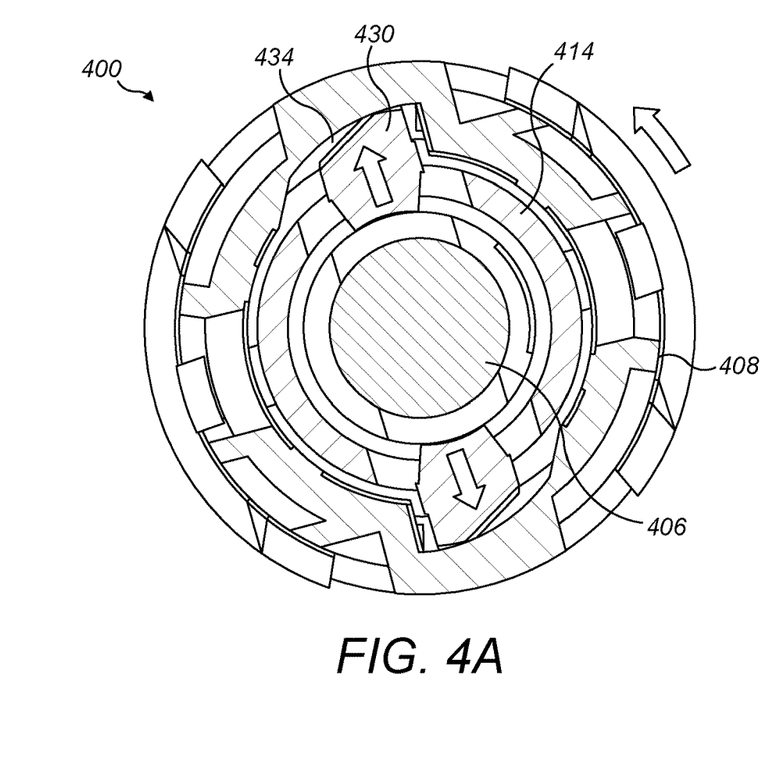
FIG. 4A shows a cross section view of an example retention mechanism for a plunger in a post-activation configuration.
Figure 4B:
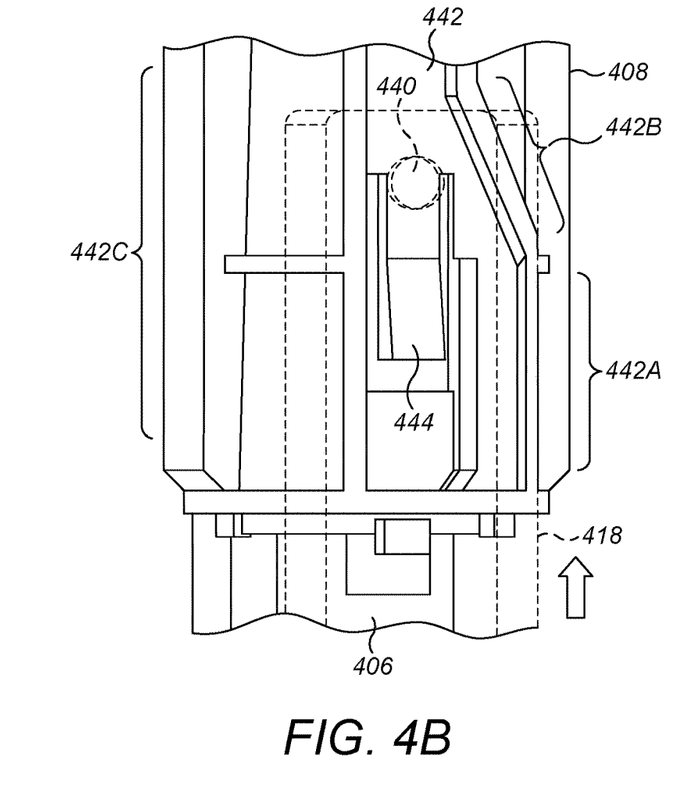
FIG. 4B shows a side view of the outside of an example retention mechanism for a plunger in a post-activation configuration.

The cam track 342 is configured to guide the shroud pin 340 from an initial position (as shown in FIG. 3B) to a hold position (as shown in FIG. 4B) during retraction of the needle shroud 318 into the injection device body. The cam track includes an initial portion 342A (also referred to herein as the "first portion") containing the initial position of the shroud pin 340. The initial portion 342A of the cam track 342 is aligned with the longitudinal axis of the injection device. The initial portion 342A of the cam track 342 provides a retention mechanism for preventing rotation of the rotatable collar 308 in the pre-use configuration, i.e., by preventing rotation of the collar 308 relative to the injection device body under the torque provided by the teeth and collar recesses, as described in relation to FIG. 3A. While in the initial portion 342A of the cam track 342, the shroud pin 340 acts as a barrier to the rotation of the collar 308, contacting a side wall (also referred to as an "edge") of the initial portion 342A of the cam track 342 to prevent rotation of the collar 308 relative to the injection device body.

The cam track 342 further includes an angled portion 342B (also referred to herein as a "second portion") that is angled with respect to the longitudinal axis of the injection device. The angled portion 342B is configured to apply a rotation force to the rotatable collar when contacted by the shroud pin 340 during retraction of the needle shroud 318, i.e., to convert a force from the shroud pin 340 in the proximal direction into a torque on the rotatable collar 308. This may be achieved by a ramped surface of the cam track 342.

The rotation force (i.e., torque) applied by the interaction of the shroud pin 340 and the angled portion 342B of the cam track 342 is in the same direction as the rotation force applied to the collar 308 by the teeth 330. The transition between the initial portion 342A and the angled portion 342B is activation/activated position; when the shroud pin 340 passes this point during retraction of the needle shroud 318, rotation of the collar 308 is no longer prevented and the collar 308 is free to rotate.

To activate the injection device, a user retracts the needle shroud 318 into the injection device body, for example by pushing the needle shroud 318 against an injection site of a subject's body. During retraction of the needle shroud 318 into the injection device body, the shroud pin 340 initially moves along the first portion 342A of the cam track 340 until it reaches the angled portion 342B of the cam track 340. Once the shroud pin 340 is in contact with the angled portion 342B, further retraction of the needle shroud 318 causes the shroud pin 340 to apply a force to the angled portion 342B of the cam track 340, which is converted to a torque on the collar 308 by the angled portion 342B of the cam track 340. The combination of the torque applied by the shroud pin 340 and the teeth 330 causes the collar 308 to rotate as the needle shroud is retracted further until the shroud pin reaches a hold position in a final portion 332C of the cam track 332.

As a result of the torque applied by the teeth 330 to the collar 308, the force required by a user to cause the collar 308 to rotate during retraction of the needle shroud 318 is reduced. This reduces the activation force of the injection device during the collar 308 rotation part of the activation process.

FIG. 4A shows a cross section view of an example retention mechanism 400 for a plunger 406 in a post-activation configuration, i.e., in a hold position.

As the rotatable collar 408 rotates, deeper parts of the collar recess 434 come into alignment with the corresponding tooth 430. The tooth 430 can then move outwards in the radial direction under the force applied by the plunger 406 (as described in relation to FIG. 2), i.e., move into the deeper pat of the collar recess 434. The deeper parts of the recess 434 effectively provide space for the rear casing clips to flex out into. This releases the plunger 406, allowing the injection to proceed.

FIG. 4B shows a side view of the outside of an example retention mechanism 400 for a plunger 406 in a post-activation configuration, i.e., in the hold position.

The cam trach 342 further includes a final portion 342C. The final portion 432C of the cam track is aligned with the longitudinal axis of the injection device, i.e., in the same direction as the first portion of the cam track 432 but offset in the angular direction around the rotatable collar 308. The final portion 432C of the cam track 432 extends further in the axial direction than the initial portion 432A of the cam track. In some examples, the final portion 432C of the cam track 432 extends further in the axial direction than the angled portion 432B of the cam track.

In some examples, the final portion 442C of the cam track 442 includes a locking mechanism 444 for locking the needle shroud 418, i.e., preventing the needles shroud 418 from being retracted again after use. The locking mechanism 442 may, for example include a one-way clip.

In the hold position, the shroud pin 440 is in a proximal part of a final portion 432C of the cam track 432. During extension of the needle shroud 418 from the injection device body under the force of the control spring, the shroud pin 440 moves in the distal direction along the final portion 442C of the cam track 442 until it reaches a final position, e.g., is in contact with a base edge of the final portion 442C of the cam track 442. In some examples, as the shroud pin 440 passes over the locking mechanism 444, it depresses a clip into the collar. Once the shroud pin 440 has passed the clip, the clip returns to its original position, and provides a barrier for preventing the shroud pin 440 moving back up the final portion 432C of the cam track 432.

Figure 5:
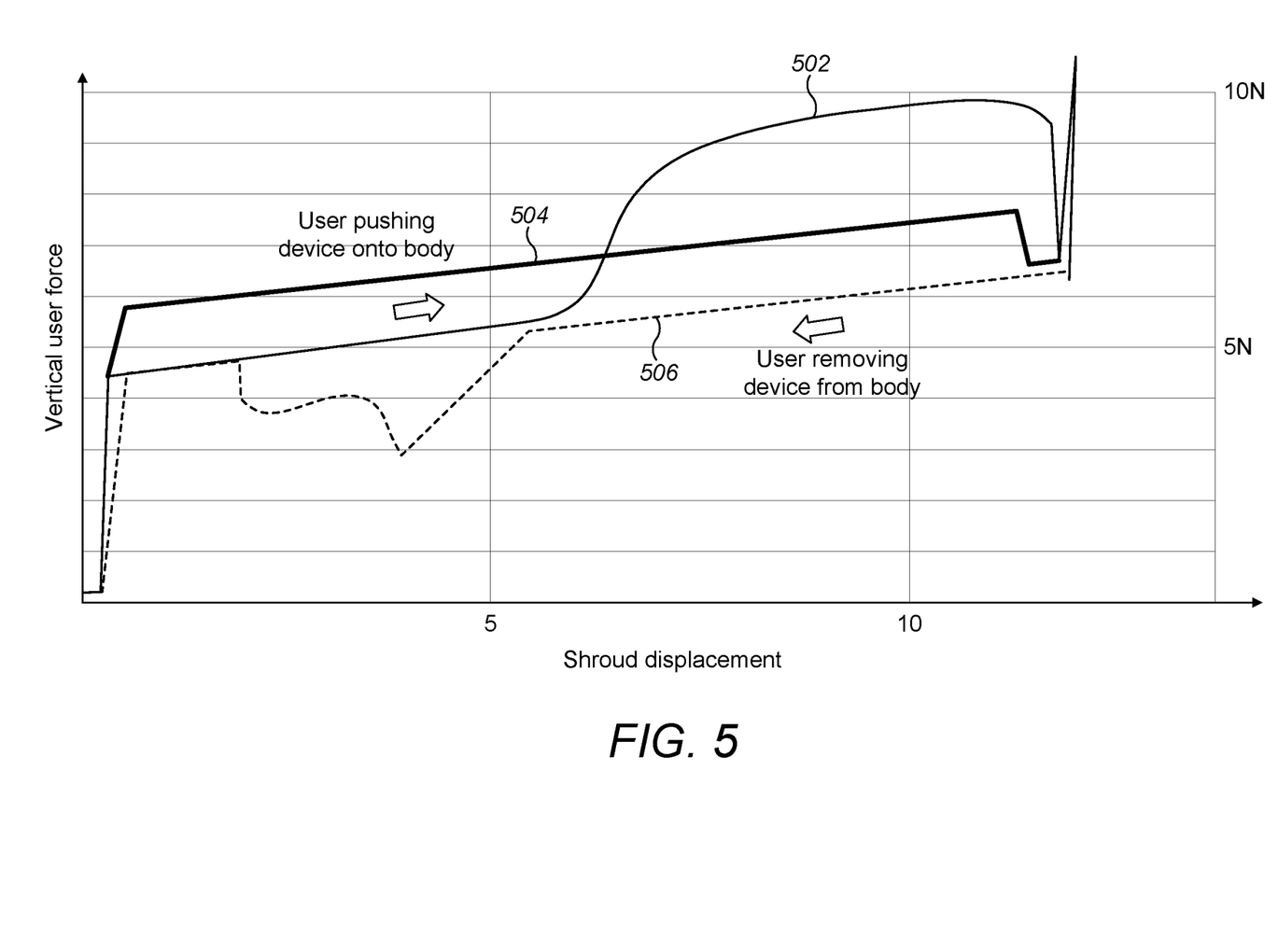
FIG. 5 shows an example comparison of force profiles of an injection device during use.

FIG. 5 shows an example comparison 500 of force profiles of an injection device during use. The graph shows a vertical force applied (in Newtons, N) by a user as a function of needle shroud displacement (in mm) during insertion and removal of the device from a subject's body for both a prior art injection device (e.g., using a prior art needle locking mechanism) and a device using a collar as described herein.

The first trace 502 shows the force profile of the activation force of a prior art device when a user is pushing the device onto a subject's body. The second trace 504 shows the force profile of the activation force of an injection device 100 according to embodiments of the present disclosure, when the user is pushing the device onto a subject's body. The third trace 506 shows the force profile of both a prior art device and an injection device 100 according to embodiments of the present disclosure when a user is removing the device 110 from a subject's body.

The first trace 502 initially has a relatively flat profile, corresponding to compression of the control spring by the shroud retracting. In this phase of the shroud retraction, the shroud pin moves along the initial part of the cam track. As the shroud pin contacts the angled part of the cam track, the force required by the user to retract the needle shroud further increases as the user force must now both compress the control spring and apply a rotation force to the collar, using the shroud pin and angled part of the cam track. The required user force decreases again once the collar has rotated, as the user then only needs to overcome the control spring force.

The second trace 504 maintains a relatively flat profile throughout the retraction of the needle shroud. The initial user force required to retract the needle shroud is slightly increased with respect to the first trace 502, since the user has to overcome both the control spring and friction between the shroud pin and the edge of the cam track. However, the user force required to cause rotation of the collar is significantly reduced due to the rotation force applied by the biased plunger via the toothed beams of the rear casing. Thus, the maximum force (i.e., the peak force) applied by the user during activation of the injection device is reduced.

The third trace 506 shows a force profile during extension of the needles shroud from the injection device. The force profile is the same for both a prior art device and a device according to the embodiments described herein.

Figure 6:
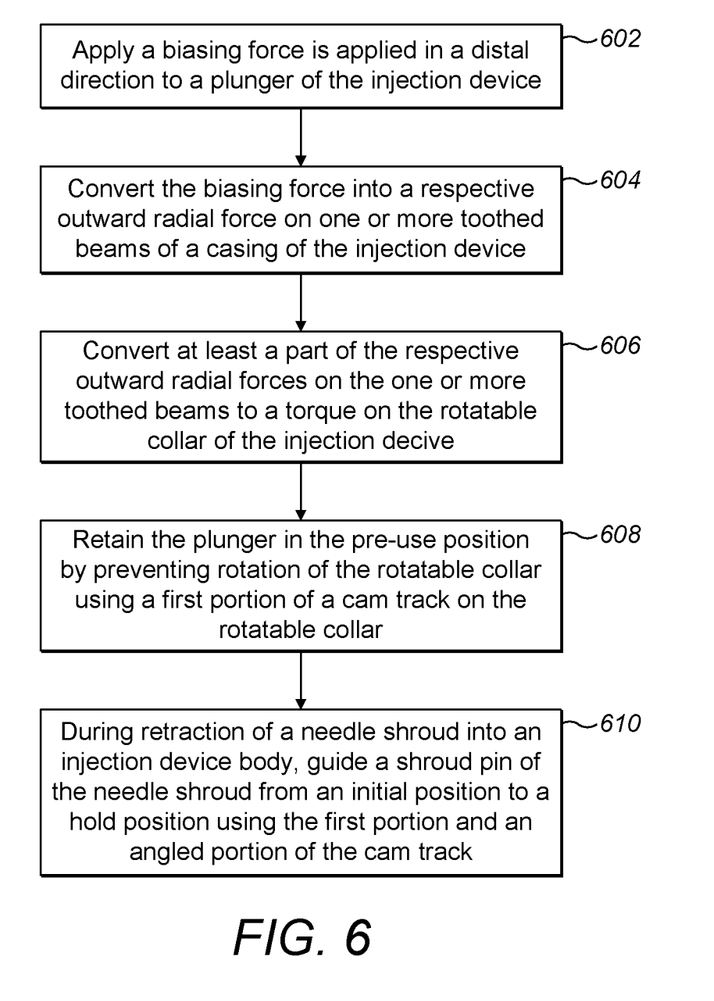
FIG. 6 shows a flow diagram of an example method for reducing the peak activation force of an injection device.

FIG. 6 shows a flow diagram of an example method for activating an injection device. The method reduces the peak activation force of the injection device, such as the injection device described in relation to FIGS. 1 to 4B.

The method starts with the injection device in a pre-use configuration, i.e., with the needle shroud extended and the shroud pin in an initial position in the cam track of the rotatable collar.

At operation 602, a biasing force is applied in a distal direction to a plunger of the injection device. The biasing force may, for example, be applied by a drive spring of the injection device.

At operation 604, the biasing force is converted into a respective outward radial force on one or more toothed beams of a casing of the injection device. One or more recesses of the plunger cooperate with a respective one or more teeth of the toothed beams to convert the force on the plunger into an outward force on the toothed beams.

At operation 606, at least a part of the respective outward radial forces on the one or more toothed beams is converted to a torque on the rotatable collar of the injection device. One or more collar recesses act in cooperation with a respective one or more of the teeth of the toothed beams to convert the radial force on the teeth into a torque on the rotatable collar.

At operation 608, the plunger is retained in the pre-use position by preventing rotation of the rotatable collar using a first portion of a cam track on the rotatable collar. An edge of the first portion of a cam track may contact a shroud pin of a non-rotatable needle shroud, thereby preventing rotation of the collar.

At operation 610, during retraction of a needle shroud into an injection device body, a shroud pin of the needle shroud is guided from an initial position to a hold position using the first portion and an angled/ramped portion of the cam track, the guiding causing the rotatable collar to rotate relative to an injection device body. The rotation of the rotatable collar causes one or more collar recesses to align with the respective one or more teeth of the toothed beam, providing space for the toothed beams to flex outwards, thereby releasing the plunger.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—injection device body/outer casing
104—medicament cartridge
106/206/306/406—plunger
108/308/408—collar
110—cap
112—longitudinal axis
114/214/314/414—rear casing
116—needle
118/318/418—needle shroud
120—control spring
122—drive spring
200/300/400—retention mechanism
226—toothed beam/rear casing clip
228—flexible arm
230/330/430—tooth
232/332/432—plunger recess
234—biasing force
334—collar recess
336—ramped contact surface of tooth
338—ramped contact surface of collar recess
340/440—shroud pin
342/442—cam track
342A/442A—initial portion of cam track
342B/442B—angled portion of cam track
442C—final portion of cam track
444—locking mechanism

The invention claimed is:
1. An injection device comprising:
an injection device body;
a plunger comprising one or more plunger recesses;
biasing means for applying a biasing force to bias the plunger in a distal direction of the injection device;
a casing at least partially enclosing the plunger, the casing comprising one or more toothed beams each comprising a tooth engageable with a corresponding plunger recess of the one or more plunger recesses; and
a rotatable collar at least partially enclosing the casing and comprising one or more collar recesses on an inner surface of the rotatable collar; and
wherein:
each of the one or more plunger recesses is shaped to urge the tooth of the corresponding toothed beam outwards when the biasing force is applied to the plunger in a pre-use configuration; and
the one or more collar recesses are shaped to cooperate with a tooth of the corresponding toothed beam to apply a torque to the rotatable collar when the corresponding toothed beam is urged outwards in the pre-use configuration.

2. The injection device of claim 1:
   wherein the rotatable collar further comprises a cam track on an outer surface of the rotatable collar;
   wherein the injection device further comprises a needle shroud retractable into the injection device and comprising a shroud pin engageable with the cam track of the rotatable collar; and
   wherein the cam track is shaped to guide the shroud pin from an initial position to a hold position and cause the collar to rotate relative to the injection device body during retraction of the needle shroud.

3. The injection device of claim 2, wherein the cam track comprises an initial portion aligned with the biasing force direction and comprising a retaining edge arranged to contact the shroud pin in the pre-use position to prevent rotation of the collar with respect to the plunger and/or casing.

4. The injection device of claim 3, wherein the cam track comprises an angled portion arranged to contact the shroud pin for at least a part of the retraction of the needle shroud, thereby applying a torque to the rotatable collar during retraction of the needle shroud.

5. The injection device of claim 4, wherein the angled portion is angled with respect to a longitudinal axis of the injection device.

6. The injection device of claim 4, wherein the torque applied to the rotatable collar by the one or more collar recesses is in a same direction as the torque applied to the rotatable collar by the angled portion during retraction of the needle shroud.

7. The injection device of claim 2, wherein the cam track further comprises a final portion for guiding the shroud pin from the hold position to a final position, the final portion comprising a locking mechanism to prevent retraction of needle shroud after the shroud pin has reached the final position.

8. The injection device of claim 7, wherein the final portion is aligned with the biasing force direction.

9. The injection device of claim 1, wherein the one or more teeth of the one or more toothed beams are chamfered in the distal direction.

10. The injection device of claim 1,
   wherein each tooth extends inwardly in a radial direction from the respective toothed beam; and
   wherein an outside surface of each tooth is chamfered in an axial direction to form a tooth contact surface for contacting the recess in the pre-use configuration.

11. The injection device of claim 10, wherein the one or more collar recesses each comprises a collar contact surface for contacting the tooth contact surface of the respective tooth in the pre-use configuration.

12. The injection device of claim 11, wherein each collar contact surface comprises a curved surface that has a radial depth that increases in the opposite direction to the rotation direction of the collar.

13. The injection device of claim 1, wherein the one or more plunger recesses comprise a curved edge at a proximal end of the plunger recess.

14. The injection device of claim 1, wherein:
   the one or more plunger recesses comprises a plurality of plunger recesses arranged evenly around the plunger in an angular direction;
   the one or more toothed beams comprises a corresponding plurality of toothed beams arranged evenly around the casing in the angular direction; and
   the one or more collar recesses comprises a corresponding plurality of collar recesses arranged evenly around the inside surface of the collar in the angular direction.

15. The injection device of claim 1, wherein the injection device further comprises a needle for expelling medicament from a medicament cartridge.

16. The injection device of claim 1, wherein the injection device further comprises a medicament cartridge containing a medicament.

17. The injection device of claim 1, wherein the plunger recesses extend through the plunger.

18. The injection device of claim 1, wherein rotation of the needle shroud with respect to the injection device body is restricted.

19. A method for reducing a peak activation force of an injection device, the method comprising:
   in a pre-use configuration of the injection device:
      applying a biasing force in a distal direction to a plunger of the injection device;
      converting the biasing force into a respective outward radial force on one or more toothed beams of a casing of the injection device using a corresponding one or more recesses of the plunger in cooperation with a respective one or more teeth of the toothed beams;
      converting at least a part of the respective outward radial forces on the one or more toothed beams to a torque on a rotatable collar of the injection device using one or more collar recesses in cooperation with a respective one or more of the teeth of the toothed beams; and
      retaining the plunger in the pre-use position by preventing rotation of the rotatable collar using a first portion of a cam track on the rotatable collar;
   during retraction of a needle shroud into an injection device body, guiding a shroud pin of a needle shroud from an initial position to a hold position using the first portion of the cam track and a ramped portion of the cam track, the guiding causing the rotatable collar to rotate relative to an injection device body,
   wherein rotation of the rotatable collar causes one or more collar recesses to align with the respective one or more teeth of the toothed beam, thereby releasing the plunger.

20. The method of claim 19, wherein the cam track comprises an initial portion aligned with the biasing force direction and comprising a retaining edge arranged to contact the shroud pin in the pre-use position to prevent rotation of the collar with respect to the plunger and/or casing.

21. The method of claim 20, wherein the cam track comprises an angled portion arranged to contact the shroud pin for at least a part of the retraction of the needle shroud, thereby applying a torque to the rotatable collar during retraction of the needle shroud.

22. The method of claim 20, wherein the method further comprises:
   guiding the shroud pin from the hold position to a final position using a final portion of the cam track; and
   locking the shroud pin at the final position using a locking mechanism to prevent retraction of needle shroud after the shroud pin has reached the final position.

23. The method of claim 19, wherein the biasing force is applied using a drive spring of the injection device.

24. The method of claim 19, further comprising expelling, by the plunger after the plunger is released, medicament from a medicament cartridge of the injection device.

25. An injection device comprising:
   an injection device body;
   a plunger comprising one or more plunger recesses;

biasing means for applying a biasing force to bias the plunger in a distal direction of the injection device;

a casing at least partially enclosing the plunger, the casing comprising one or more toothed beams each comprising a tooth engageable with a corresponding plunger recess of the one or more plunger recesses; and a rotatable collar at least partially enclosing the casing and comprising a cam track on an outer surface of the rotatable collar;

a needle shroud retractable into the injection device body and comprising a shroud pin engageable with the cam track of the rotatable collar; and wherein:

each of the one or more plunger recesses is shaped to urge the tooth of the corresponding toothed beam outwards when the biasing force is applied to the plunger in a pre-use configuration; and the cam track is shaped to guide the shroud pin from an initial position to a hold position and cause the rotatable collar to rotate relative to the injection device body during retraction of the needle shroud.

\* \* \* \* \*